US008173119B2

(12) United States Patent
Tamarat et al.

(10) Patent No.: US 8,173,119 B2
(45) Date of Patent: May 8, 2012

(54) USE OF ADIPOSE-TISSUE CELL FRACTIONS FOR POST-IRRADIATION TISSUE REGENERATION

(75) Inventors: Radia Tamarat, Paris (FR); Marc Benderitter, L'hay les Roses (FR)

(73) Assignee: Institut de Radioprotection et de Surete Nucleaire (FR)

(*) Notice: Subject to any disclaimer, the term of this patent is extended or adjusted under 35 U.S.C. 154(b) by 269 days.

(21) Appl. No.: 12/308,445

(22) PCT Filed: Jun. 12, 2007

(86) PCT No.: PCT/EP2007/055782
§ 371 (c)(1),
(2), (4) Date: Dec. 12, 2008

(87) PCT Pub. No.: WO2007/144358
PCT Pub. Date: Dec. 21, 2007

(65) Prior Publication Data
US 2010/0233134 A1     Sep. 16, 2010

(30) Foreign Application Priority Data
Jun. 12, 2006  (FR) ..................... 06 05190

(51) Int. Cl.
*A61K 35/12*  (2006.01)
*C12N 5/02*  (2006.01)
*C12N 5/74*  (2006.01)

(52) U.S. Cl. ................. 424/93.7; 435/378; 435/366
(58) Field of Classification Search ................. 435/366, 435/378; 424/93.7
See application file for complete search history.

(56) References Cited

U.S. PATENT DOCUMENTS

| 2003/0082152 A1 | 5/2003 | Hedrick et al. |
| 2005/0107876 A1 | 5/2005 | Kim et al. |

FOREIGN PATENT DOCUMENTS

| FR | 2819265 | 7/2002 |
| FR | 2859381 | 3/2005 |
| WO | 01/62901 | 8/2001 |
| WO | 02/055678 | 7/2002 |
| WO | 2005025584 | 3/2005 |
| WO | 2005035742 | 4/2005 |

OTHER PUBLICATIONS

Gonyon et al., Annals of Plastic Surgery, 50(3); 315-320 (2003). (Abstract only.).
Hopewell, Int. J. Radiat. Biol., 57(4); 751-773 (1990).
Archambeau et al., Int. J. Radiation Oncology Biol. Phys., 31(5); 1171-1185 (1995).
Omidvari et al., Net Sutdy: Topical Betamthason for Prevention of Radiation Dermatitis, 7 pages (2006). (Abstract only).
Masferrer et al., Clin. Transl. Oncol. 12; 43-48 (2010).

(Continued)

*Primary Examiner* — Rosanne Kosson
(74) *Attorney, Agent, or Firm* — Lerner, David, Littenberg, Krumholz & Mentlik, LLP

(57) ABSTRACT

The present invention concerns the use of cells derived from the cellular fraction of the vascular stroma of the extramedullary adipose tissue to promote the regeneration of tissue following lesions caused by irradiation. More specifically, the use according to the invention aims to prepare a drug for promoting regeneration of the skin, and in particular to repair the cutaneous wounds caused by irradiation.

6 Claims, 3 Drawing Sheets

OTHER PUBLICATIONS

De Vries et al., Laboratory Investigation, United States and Canadian Academy of Pathology, Baltimore,, US, 73(4); 532-540 (1992).
Gimble, Expert Opinion on Biological Therapy, Ashley, London, GB, 3(5); 705-713 (2003).
Casteilla et al., Annales De Chirurgie Plastique Esthetique, Expansion Scientifique Francaise, Paris, FR, 49(5); 409-418 (2004).
International Search Report, PCT/EP2007/055782, Aug. 30, 2007.
Bjorntorp et al., J.Lipid Res., 19; 316-324 (1978).
Truong et al., Journal of Burns and Wounds, vol. 4, 72-82 (2005).

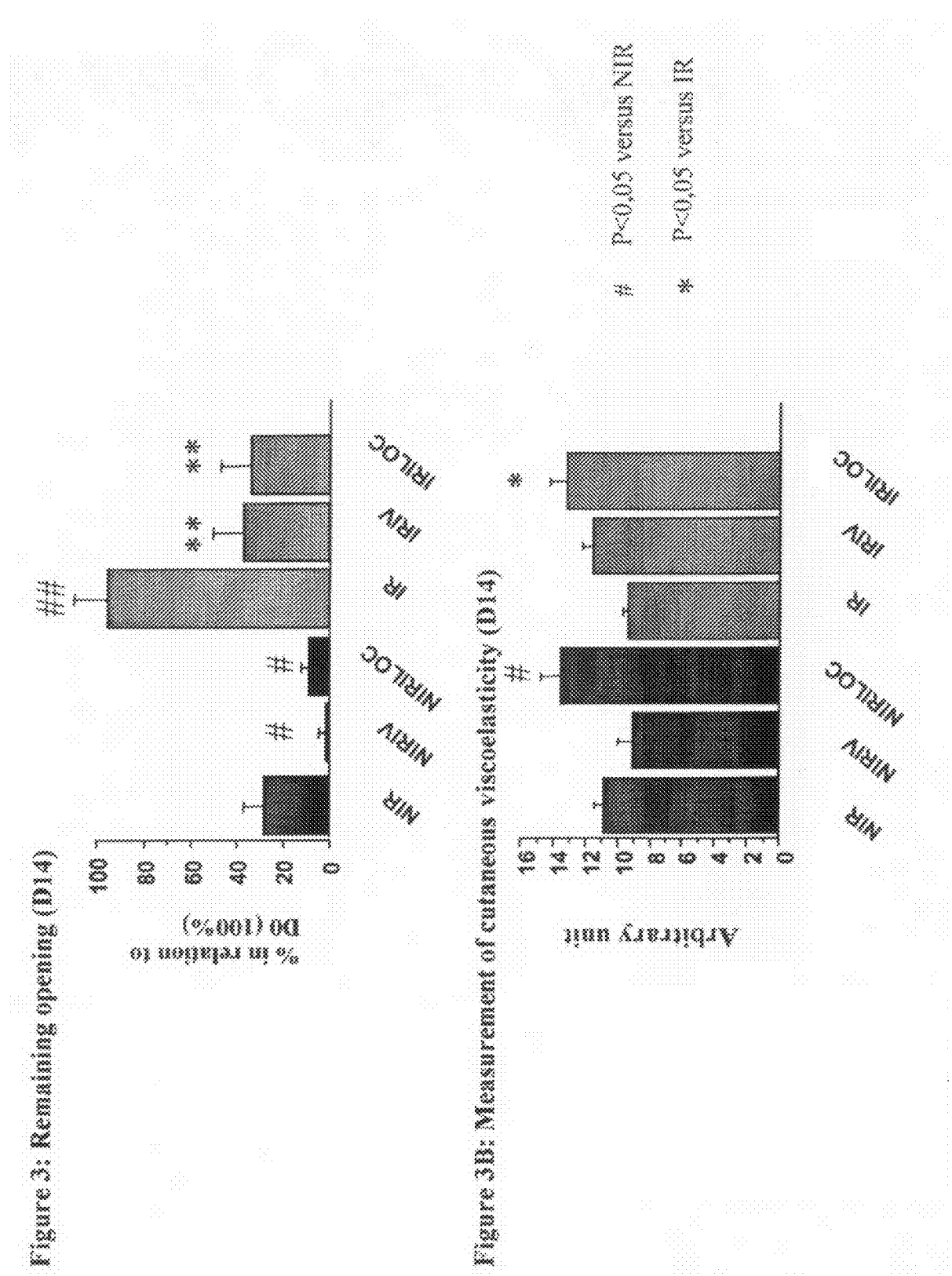

USE OF ADIPOSE-TISSUE CELL FRACTIONS FOR POST-IRRADIATION TISSUE REGENERATION

CROSS-REFERENCE TO RELATED APPLICATIONS

The present application is a national phase entry under 35 U.S.C. §371 of International Application No. PCT/EP2007/055782, filed on Jun. 12, 2007, which claims priority from French Patent Application No. 0605190 filed Jun. 12, 2006, both of which are incorporated herein by reference.

The present invention concerns the use of cells derived from the fraction of the vascular stroma of extramedullary adipose tissue to promote the regeneration of tissue following lesions caused by irradiation.

BACKGROUND OF THE INVENTION

The healing process involves a set of complex and perfectly orchestrated biological and molecular mechanisms, such as cell migration, cell proliferation or the depositing of extracellular matrix. An induced lesion constitutes the starting point for a cascade of events comprising interactions between local, regional and systemic growth factors, as well as participation at the cellular level of various elements such as bone marrow stem cells. Disruption of these complex mechanisms has incapacitating consequences for the patients, in particular physical consequences or consequences on quality of life that can be as drastic as death. This is the case when infections occur and lead, in the most serious cases, to amputation of the limbs or, more generally, to serious surgical intervention.

With regard to cutaneous lesions, a wound lead to more or less deep destruction of the tissues and to hypoxia, which leads to a regulation of growth factors, an activation of matrix destruction and a stimulation of angiogenesis. After only few hours, epidermal and dermal cell migration and proliferation constitute factors triggering re-epithelialisation. The formation of a new vascular network is also necessary to sustain newly formed tissue. Nevertheless, it has been shown that many pathological situations lead to a dysfunction in angiogenesis, loss of keratinocytes as well as impairment of skin regeneration.

Currently used therapies essentially involve surgery, at times accompanied by administration of suitable medications such as antibiotics. Therapies making use of growth factors have also been envisaged, in particular the administration of PDGF-BB and bFGF, and even cellular therapy. These therapies promote wound healing and can be used alone or to supplement other therapies or surgeries. Techniques involving regenerating cells have been relatively successful. They consist in using the capacity of stem cells to self-renew indefinitely and to become differentiated into mature specialised cells and tissues. However, these methods require cutting-edge technologies and are extremely expensive due to the availability, the obention and purification of raw materials. They are also generally very dependent on potential contamination by micro-organisms and the relatively long period of time needed for the preparation of raw materials. These cellular therapies appear to be the most promising.

Thus, application US-2003/0082152 (1) describes in a rather general manner processes for the preparation of stem cells derived from adipose tissue, as well as their multipotency and the advantages of these cells to be used in tissue engineering, wound healing and tissue regeneration in vivo and ex vivo. The type of wounds for which these cells can be used to promote healing does not include wounds of a mechanical origin. No part of this document suggests that lesions caused by irradiation can also be treated.

Similarly, De Vries et al. 1995 (2) describes the test on dermal substitutes seeded with various types of cell population on the healing of cutaneous lesions caused by mechanical problems. The cell populations tested include autologous fibroblasts, a population called the vascular stroma fraction (VSF) derived from adipose tissue as well as the same vascular stroma fraction in which vascular fragments have been removed (SF). The results obtained in this article show that dermal substituted seeded with an SF population, as well as substitutes seeded with autologous fibroblasts enable to promote the healing of cutaneous wounds caused by mechanical problems. Here again, the article neither describes nor suggests that lesions caused by irradiation, which are much more complex, can also be treated in the same manner.

As indicated previously, various pathological conditions disrupt lesion repair mechanisms. This is the case with irradiation which modifies angiogenesis and re-epithelialisation. Several studies have shown that radiation can cause dry desquamation associated with atypical skin keratinisation or epiderm loss accompanied by ulceration. Vascular changes also occur, including occlusion, oedema, thrombosis or vessel destruction. For example, at the skin level, lesions are different from those observed in the case of other wounds or pathological lesions. These phenomena trigger a slowing down of the healing process.

In particular, local irradiation of the skin affects the healing process considerably. Early lesions, thought to be caused by a delayed disorder of the proliferating basal layer of the epidermis, and late lesions, linked to disorders of the dermis and subjacent tissue, will appear after exposure to high radiation doses. The first symptom observed is radiodermatitis, defined as an inflammatory skin reaction similar to a first degree burn, followed by depilation. Dilatation of the capillaries also causes acute erythema. Finally, dry then humid desquamation can occur several days after irradiation with 10 to 20 Gray and is characterised, on the one hand, by keratinocyte degeneration in the epidermis leading to the thinning and flattening of the dermal papilla and, on the other hand, by swelling and proliferation of the vascular endothelium. The delayed effects are seen in the form of ischemia probably originating from hyper-proliferation of surviving epithelial cells causing localised or partial occlusion of the arterioles and major fibrosis. These physiological phenomena are not present in mechanically generated wound-type cutaneous lesions, which are thus of a different nature compared to those caused by irradiation.

In particular, the fact that a drug is effective in improving the healing of mechanically caused wounds does not necessarily mean that this drug is effective in the treatment of lesions, notably cutaneous, linked to irradiation, because the healing of post-irradiation lesions involves much more complex mechanisms.

In the context of post-irradiation, whether accidentally caused or resulting from radiotherapy, it is therefore highly important to be able to implement effective lesion repair mechanisms, in particular for cutaneous lesions.

Different stem cell sources have been envisaged for the implementation of cellular therapies. Initially, stem cells were isolated from embryonic tissue but recently the presence of pluripotent stem cells has been detected in various adult tissues such as bone marrow, skin, brain, muscle and adipose tissue. Such stem cells are thus more easily available than embryonic cells and their use does not involve the same ethical problems. The use of stem cells is limited by their low number in most adult tissues and by the difficulty in extracting and purifying them. New access routes have been suggested (3) for obtaining stem cells, in particular from adipose tissue.

Adipose tissue can indeed constitute an important reservoir, in which stem cells are comparatively easy to isolate in relatively large quantities. Moreover, stem cells allow to overcome the problem of donor compatibility, such a problem arising with bone marrow cells for example They also make it possible to envisage the use of "autologous-grafts" thus avoiding failures linked to potential rejections.

Adipose tissue exists in different forms in mammals, for example and extramedullary white adipose tissue, the body's main reserve organ, white medullary adipose tissue and thermogenic brown adipose tissue. White adipose tissue constitutes an abundant source of cells that are easy to obtain. In addition, its potential lasts throughout life. It consists of two cellular fractions: an adipocyte fraction characterised by the accumulation of triglycerides and consisting mainly of differentiated adipocytes, and a non-adipocyte fraction called the vascular stroma fraction (VSF) comprised of blood cells, mature endothelial cells, pericytes, fibroblasts and pluripotent stem cells. The vascular stroma fraction also includes other adipocyte progenitors, haematopoietic and neurogenic progenitors as well as mesenchymatous stem cells capable of differentiating into oestrogen, chondrogen and myogen lines (4).

White adipose tissue has angiogenic properties with applications in autologous cellular therapy in a post-traumatic or pathological context. Injection of autologous adipose tissue is used in particular during surgery to promote revascularisation of grafts and reconstruction of soft tissue. Cells derived from VSF have also been administered to promote angiogenesis in the treatment of ischemic pathologies. VSF cells represent a heterogeneous cell population surrounding the adipocytes in fatty tissue, and include mature microvascular endothelial cells. This fraction has also been identified as an important source of pluripotent cells capable of differentiating into neurogenic and cardiomyocyte phenotypes and, more recently, as possessing angiogenic activity. VSF is involved in the formation of a matrigel model and increases neovascularisation of ischemic tissue (5). Moreover, adipocyte cell lines have the capacity to release important pro-angiogenic factors such as monobutyril, vascular endothelial growth factor (VEGF) and leptin.

Use of cells derived from VSF in cellular therapy is therefore recognised to be of major interest. They have thus been proposed in the treatment of myopathy, cardiopathy and other diseases in which there is muscle degeneration. Their benefit in the reconstruction of functional vascular networks has also been studied.

SUMMARY OF THE INVENTION

In one embodiment of the present invention, cells derived from the cellular fraction of the vascular stroma of extramedullary adipose are used for the preparation of a drug aimed at promoting tissue regeneration in lesions caused by irradiation.

In another embodiment, the drug is aimed at promoting the regeneration of skin and more specifically. Keratinocytes.

In aspects of the present invention lesions treated may be located in tissue in the skin, bone, brain, neck, intestine, breasts, heart, lungs, uterus and rectum. These lesions may also include cutaneous wounds caused by irradiation. In alternative embodiments, the irradiation may be a result of radiotherapy or accidental radiation.

In another alternative embodiment of the present invention, the drug prepared may be administered as a preventive measure, prior to irradiation or as a curative measure, after irradiation. The drug may also be administered in cancer patients.

The drug of the present invention may be in the form of a cream, ointment, spray, gel, vial and/or injectable solutions.

In yet another alternative embodiment, the drug may be in the form of an equivalent dermis and this equivalent dermis may be used for the treatment of burns caused by irradiation.

DETAILED DESCRIPTION

The Applicant has surprisingly found that cells derived from the vascular stroma fraction of extramedullary adipose tissue are of considerable interest in the treatment of lesions in a specific post-irradiation context.

Thus the present invention concerns the use of cells derived from the vascular stroma fraction of extramedullary adipose tissue to prepare a drug intended to promote tissue regeneration following lesions caused by irradiation.

An advantageous aspect of the invention relates to the use of cells derived from the vascular stroma fraction of extramedullary adipose tissue to prepare a drug intended to promote skin regeneration, in particular for keratinocytes, following lesions caused by irradiation. More particularly, the lesions are cutaneous wounds caused by irradiation.

Up until now, many studies have proposed the idea of pharmacological stimulation of the healing process by administration of pro-angiogenic agents or pro-inflammatory molecules. Known cellular methods involve the use of bone marrow cells or of blood cells. In this context of post-irradiation pathological healing, cells derived from adipose tissue have never been used.

Lesions and more particularly wounds and/or skin burns caused by irradiation, whether accidental or as a result of radiotherapy treatment, differ in nature from physiopathological trauma. The epidermis and keratinocytes are affected, tissue elasticity is reduced and the healing process is considerably slower.

The use of cells derived from the VSF of extramedullary adipose tissue acts by accelerating wound closure by acting at the level of keratinocyte differentiation and/or skin viscoelasticity, in particular by increasing the production of collagen. This has the advantage of giving a large quantity of tissues and cells and does not pose any particular ethical problems. It is moreover possible to envisage homologous or heterologous grafts and the possibility of treating several persons from a single individual. Implementation of the use according to the invention is made greatly easier by the source of the tissues used. It is indeed possible to maintain, multiply and even immortalise cells in vitro in a given medium. Freezing the cells can be envisaged in order to make cell pools available.

As lesions, and, more particularly, cutaneous lesions, are repaired much more quickly when used according to this invention, tissues are protected more quickly against external pathogenic agents.

The advantages in terms of costs are also considerable. Obtaining stem cells is easier because of their origin and the protocols are more straightforward and less expensive. As a matter of fact, many samples can be taken, notably during liposuction or dermolipectomy, those samples being usually destroyed. Sampling methods are not very invasive and as a result hospital and care time are much shorter. All these factors contribute to reducing the cost of the treatment described above.

Another aspect of this invention concerns the use of cells derived from the vascular stroma fraction of extramedullary adipose tissue to promote tissue regeneration following lesions caused by irradiation in tissues chosen among skin, bone, brain, neck, intestine, breasts, heart, lungs, uterus and rectum.

The use of cells derived from the vascular stroma fraction of extramedullary adipose tissue according to this invention can be applied to many fields. Lesions can be caused by accidental irradiation or as a result of radiotherapy treatment. This is particularly true in the case of cancer patients.

The drugs used within the scope of this invention can be used preventively and administered prior to irradiation. They can of course also be used curatively and administered after irradiation.

Cells derived from adipose tissue are obtained directly from adipose tissue fragments taken under anaesthesia. After enzyme digestion of the extracellular matrix, various cell populations are selected by density difference or antigen expression difference.

The adipocyte-free vascular stroma fraction used to implement this invention is thus isolated.

According to an advantageous embodiment of the invention, the cells are obtained via the following successive steps:
  removal of a sample of an extramedullary adipose tissue,
  isolation according to the procedures described by Bjorntorp et al. (6) of the vascular stroma fraction by matrix digestion using proteolytic enzymes and separation by means of a density gradient,
  purification of the cells by physical separation and/or by immunoselection.

The physical separation is carried out by means of adhesion differences on a solid support while the immunoselection is carried out using several antibodies that are specific for markers expressed by the adipocyte precursors (CD 34+, CD45− and CD31−).

Cells derived from the VSF of extramedullary adipose tissue are used, according to the invention, to prepare a drug in the form of a pharmaceutical composition containing cells derived from the vascular stroma fraction of extramedullary adipose tissue and at least one pharmaceutically acceptable vehicle and/or support. This pharmaceutical composition is adapted to any of the usually used forms of administration. The pharmaceutical forms include more particularly those suited to parenteral, per or transcutaneous administration, creams, ointments, sprays, gels, vials and/or injectable solutions. The dosage varies as a function of patient age and weight, administration route and any associated treatment.

In one aspect of the invention, the use of the cells derived from the vascular stroma fraction of extramedullary tissue is aimed at preparing a drug in the form of a spray, gel or injectable solution. In particular, these pharmaceutical compositions can be in the form of aerosols.

In another aspect of the invention, the cells derived from the vascular stroma fraction of extramedullary adipose tissue are used to prepare dermal substitutes such as INTEGRA® and are aimed at promoting tissue regeneration following lesions caused by irradiation. Dermal substitutes are aimed at administrating the cells in a collagen matrix constituting INTEGRA®. The polymer or co-polymer support is solid or semi-solid.

INTEGRA® is an artificial skin or cutaneous regeneration structure. It is a double layer membrane system aimed at replacing the skin. The dermal replacement layer is produced in particular from a porous matrix of reticulated collagen fiber from bovine tendon and from a glycosaminoglycan whose porosity is controlled and whose rate of degradation is defined during production.

More particularly, according to this aspect, dermal substitutes are useful in the treatment of burns caused by irradiation.

The following examples illustrate the invention but in no way limit it.

BRIEF DESCRIPTION OF THE DRAWINGS

FIG. 3: Histograms of wound-opening measurements remaining at D 14 (FIG. 3A) and viscoelasticity at D 14 (FIG. 3B).

EXAMPLE 1

Obtaining and Preparing Adipose Tissue

An adipose tissue fragment is removed from subcutaneous adipose tissue taken from anaesthetised mice. After digestion of the extracellular matrix by proteolytic enzymes at 37° C. in collagenase for 45 minutes, to allow dissociation of tissue cells, various cell populations are selected by density difference according to the procedure described by Bjorntorp et al (6) or by the difference in antigen expression. The cell fraction that does not contain adipocytes corresponds to the vascular stroma fraction. Cells are labelled with CD34+, CD45− and CD31.

EXAMPLE 2

Effect of Cell Fractions According to the Invention on Healing

Localised irradiation with 20 Gy is carried out on the dorsal side of the mouse after shaving and anaesthetisia. Irradiation is carried out prior to application of a punch.

Wound Healing Model:

A 0.8 mm diameter punch is applied to the dorsal side of 8-week-old male mice (C57B16, Iffa Creddo) in order to produce a wound. Immediately after application of the punch, the cells obtained in Example 1 are injected locally (loc) or intravenously (iv). Animals receive $1 \times 10^6$ cells and controls receive the solvent (saline phosphate buffer).

Each experiment group includes 5 individuals.

The experiments are repeated without preliminary irradiation of mice.

Figure 1:
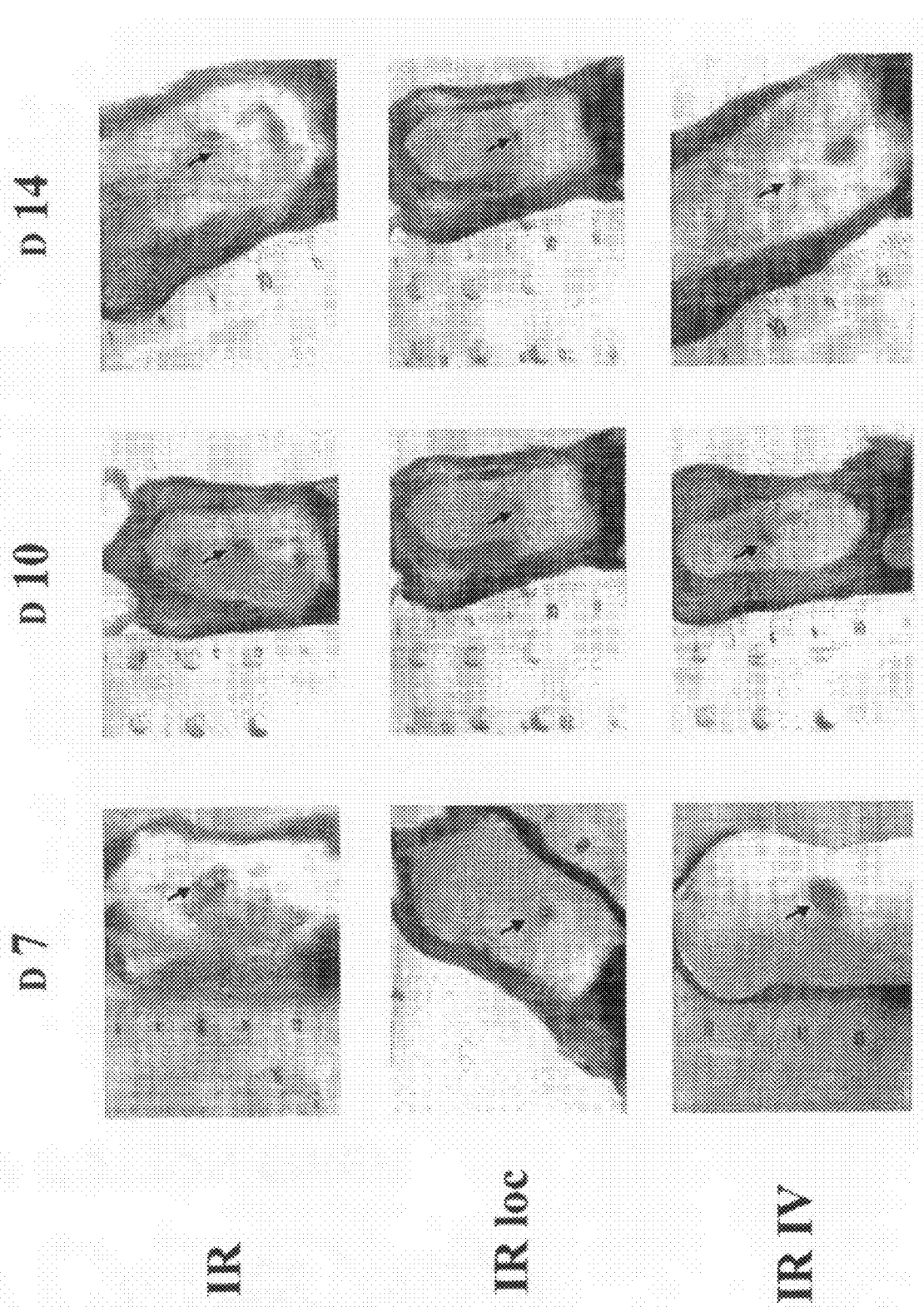
FIG. 1: Observation of wound healing evolution changes in mice in a pathological, post-irradiation context.
Figure 2:
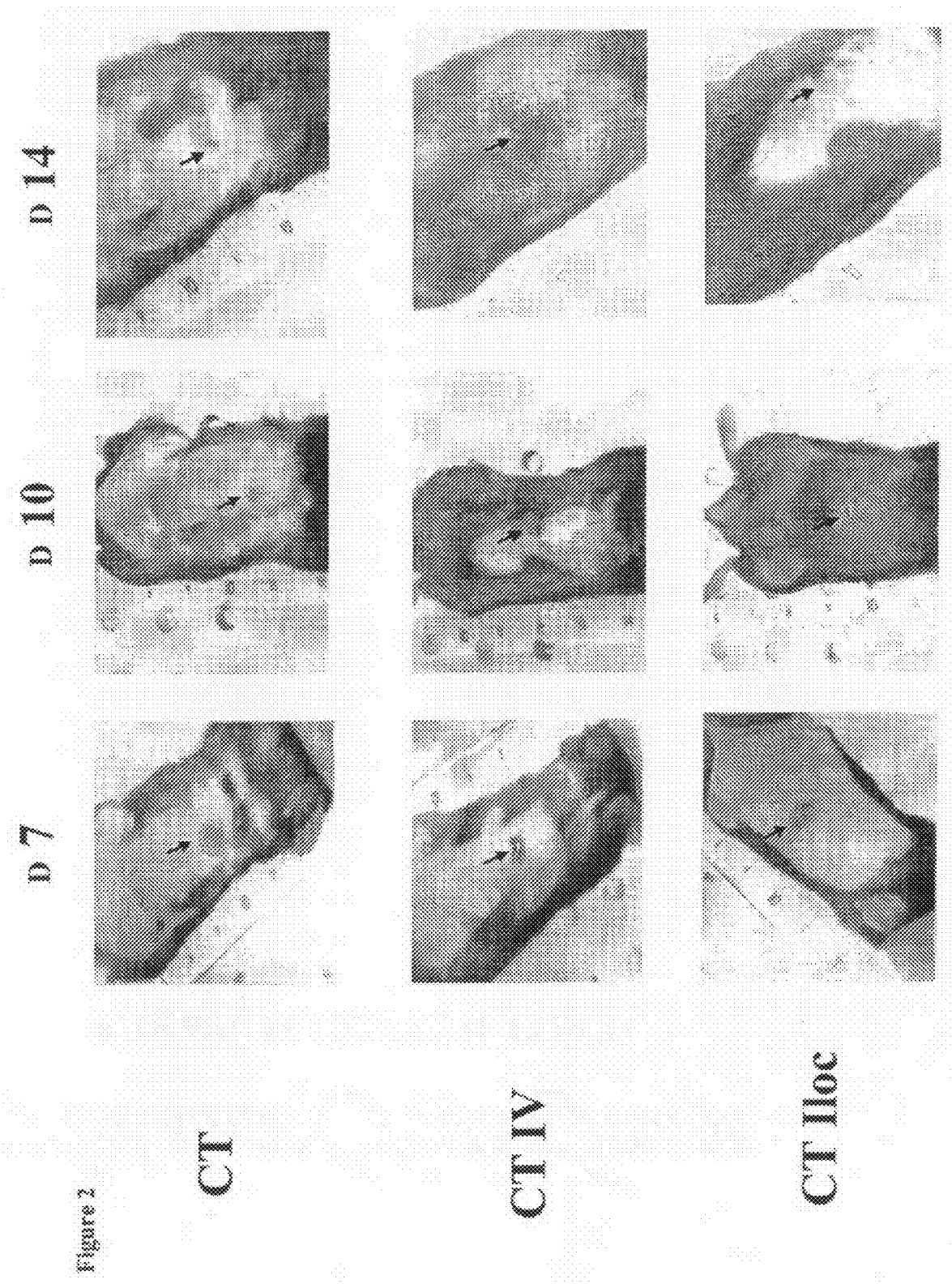
FIG. 2: Observation of wound healing evolution in mice in a physiological context without irradiation.

Technical Evaluation of Wound Healing:

The reduction in wound surface area is evaluated by direct observation at different times (D0, D4, D7, D10 and D14). Changes in the wounds of mice are monitored photographically. The results are reported in FIG. 1 (IR, IR Loc, IR iv). These observations are compared with changes in the same wound carried out in a physiological context (CT, CT loc, CT iv), in other words without preliminary irradiation (refer to FIG. 2).

Surface measurements are carried out using image analysis software (Histolab) under two sets of wound healing conditions: physiological and pathological. They are reported in Table I below which gives the values of wound openings remaining at D14. These values are expressed as the remaining percentage with respect to D0 set as 100%.

TABLE I

| | Context | | | | | |
|---|---|---|---|---|---|---|
| | Pathology Irradiation | | | Physiology Without irradiation | | |
| Animals | Control | I loc | I i.v | Control | I loc | I i.v |
| 1 | 24.9 | 7.7 | 11.9 | 6.3 | 0.7 | 1.5 |
| 2 | 55 | 3.7 | 8.6 | 23.8 | 0.3 | 6.2 |
| 3 | 31.5 | 10.59 | 6.7 | 10.5 | 0.3 | 3.2 |
| 4 | 44.9 | 7.34 | 5.3 | 4.7 | 0.8 | 1.4 |
| 5 | 44.15 | 45.1 | 34.8 | 11.1 | 0.8 | 5.7 |
| Mean | 37.4 | 14.8 | 13.4 | 11 | 0.58 | 3.6 |
| Standard deviation | 5.3 | 7.6 | 5.4 | 4.3 | 0.1 | 1 |

The corresponding histograms are given in FIG. 3A.

Measurement of Healing Quality Using a Cutometer Technique:

The aim of this measurement is to verify that tissue regeneration is associated with an improvement in tissue quality. At the end of the healing process, a 2 mm probe is applied to aspirate the dorsal skin of animals and estimate the cutaneous viscoelasticity parameter in regenerated tissue. The appliance of the probe allows to aspirate and relax the skin. Skin deformation is estimated using an optical measurement system which provides a graph with skin elasticity and relaxation measurements. In the same way as previously, measurements are carried out in parallel in a pathological context on irradiated animals and in a physiological context on animals not subjected to preliminary irradiation.

The results of viscoelasticity measurements are reported in Table II below and expressed in arbitrary units.

TABLE II

| | Context | | | | | |
|---|---|---|---|---|---|---|
| | Pathology Irradiation | | | Physiology Without irradiation | | |
| Animals | Contrôle | I loc | I i.v | Contrôle | I loc | I i.v |
| 1 | 6.9 | 14.7 | 10.7 | 12.7 | 14.7 | 6.9 |
| 2 | 8.83 | 12.3 | 13.99 | 11.8 | 12.3 | 10.1 |
| 3 | 9.4 | 17.2 | 10 | 12.6 | 17.2 | 12 |
| 4 | 10 | 13.2 | 11.5 | 9 | 13.2 | 9.3 |
| 5 | 11.6 | 10.42 | 11.7 | — | 10.42 | 6.9 |
| Mean | 9.34 | 13.36 | 11.57 | 11.4 | 13.56 | 9.04 |
| Standard deviation | 1.71 | 1.14 | 0.6 | 0.8 | 1.1 | 0.9 |

The corresponding histograms are given in FIG. 3B.

In the absence of VSF cells from extramedullary adipose tissue, tissue repair in a post-irradiation context takes place in a delayed manner and reconstitution is only partial. As a matter of fact, at the end of the process (D14), there is still a large open wound area.

Mice having received VSF cells from extramedullary adipose tissue had completely reconstituted skin with complete wound closure and an improvement in the quality of skin and more particularly in its viscoelasticity.

The slowing down observed in the closure of wounds in a post-irradiation context completely disappears with the use of VSF cells derived from extramedullary adipose tissue according to the invention and the values observed show that the acceleration in the healing process after administration of these cells in an irradiation context results in a wound similar to that observed in a normal physiological healing situation.

The invention claimed is:

1. A method for treating one or more skin lesions caused by radiation therapy, the method comprising the administration of a cell preparation comprising an effective amount of cells derived from the cellular fraction of the vascular stroma of extramedullary adipose tissue to the lesions of a patient in need thereof by local or intravenous administration, wherein the cellular fraction of the vascular stroma is the vascular stromal fraction (VSF fraction).

2. The method according to claim 1, wherein the cells in the VSF fraction promote regeneration of keratinocytes.

3. The method according to claim 1, wherein the patient is a cancer patient.

4. The method according to claim 1, wherein the cells are administered in the form of one or more of a cream, ointment, spray, gel or injectable solution.

5. The method according to claim 1, wherein the cells are administered in the form of a dermal substitute.

6. The method according to claim 5, wherein the one or more lesions are burns.

* * * * *

UNITED STATES PATENT AND TRADEMARK OFFICE
CERTIFICATE OF CORRECTION

| | | |
|---|---|---|
| PATENT NO. | : 8,173,119 B2 | Page 1 of 1 |
| APPLICATION NO. | : 12/308445 | |
| DATED | : May 8, 2012 | |
| INVENTOR(S) | : Radia Tamarat et al. | |

It is certified that error appears in the above-identified patent and that said Letters Patent is hereby corrected as shown below:

In the Specification

Column 3, Line 53, "SUMMARY OF THE INVENTION" should read --BRIEF SUMMARY OF THE INVENTION--

Column 4, Line 9, "the form of an equivalent dermis and this equivalent dermis" should read --the form of a dermal substitute and this dermal substitute--

Signed and Sealed this
Eleventh Day of March, 2014

Michelle K. Lee
*Deputy Director of the United States Patent and Trademark Office*